US006884252B1

(12) United States Patent
Urich et al.

(10) Patent No.: US 6,884,252 B1
(45) Date of Patent: Apr. 26, 2005

(54) LOW FREQUENCY CATARACT FRAGMENTING DEVICE

(75) Inventors: Alex Urich, Mission Viejo, CA (US); Michael Curtis, Lake Forest, CA (US)

(73) Assignee: Circuit Tree Medical, Inc., Mission Viejo, CA (US)

( * ) Notice: Subject to any disclaimer, the term of this patent is extended or adjusted under 35 U.S.C. 154(b) by 0 days.

(21) Appl. No.: 09/542,670

(22) Filed: Apr. 4, 2000

(51) Int. Cl.⁷ .................................................. A61F 9/00
(52) U.S. Cl. ...................................... 606/166; 604/22
(58) Field of Search ........................ 606/159, 114, 171, 606/169, 166, 177, 178; 604/22, 20, 268

(56) References Cited

U.S. PATENT DOCUMENTS

| | | | | |
|---|---|---|---|---|
| 3,673,475 A | * | 6/1972 | Britton, Jr. ................... 318/122 |
| 4,024,866 A | * | 5/1977 | Wallach ........................ 604/31 |
| 4,911,161 A | * | 3/1990 | Schechter .................... 606/107 |
| 5,196,006 A | * | 3/1993 | Klopotek et al. ............. 606/32 |
| 5,383,460 A | * | 1/1995 | Jang et al. ................... 600/439 |
| 5,425,704 A | * | 6/1995 | Sakurai et al. ................ 604/22 |
| 5,897,569 A | * | 4/1999 | Kellogg et al. ............. 606/169 |
| 6,027,515 A | * | 2/2000 | Cimino ...................... 606/169 |
| 6,165,190 A | * | 12/2000 | Nguyen ...................... 606/166 |
| 6,258,111 B1 | * | 7/2001 | Ross et al. .................. 606/171 |
| 6,261,297 B1 | * | 7/2001 | Kadziauskas et al. ....... 606/107 |
| 6,425,883 B1 | * | 7/2002 | Urich et al. ................. 604/119 |

\* cited by examiner

*Primary Examiner*—Julian W. Woo
*Assistant Examiner*—Victor Nguyen
(74) *Attorney, Agent, or Firm*—Irell & Manella LLP

(57) ABSTRACT

A control circuit that provides a driving signal to a transducer coupled to a mechanical cutting element. The transducer is capable of operating in a resonant mode. The driving signal contains a plurality of pulses provided in a time interval that does not cause the transducer to operate in the resonant mode.

21 Claims, 2 Drawing Sheets

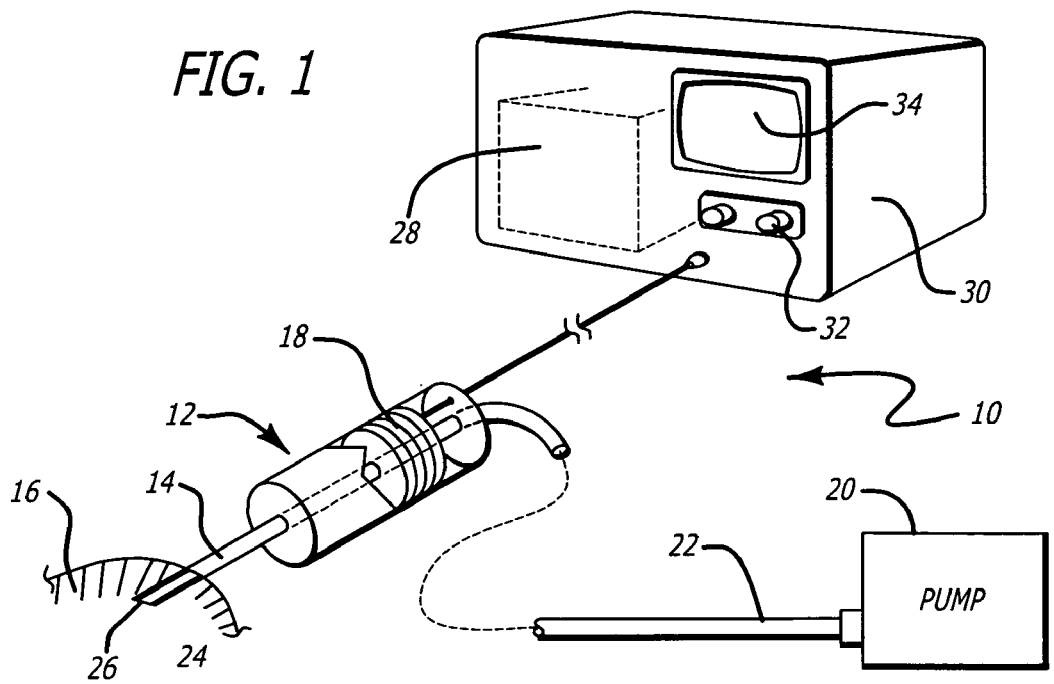

LOW FREQUENCY CATARACT FRAGMENTING DEVICE

BACKGROUND OF THE INVENTION

1. Field of the Invention

The present invention relates to a control circuit for driving a transducer that is coupled to a mechanical cutting element.

2. Prior Art

The lens of a human eye may develop a cataracteous condition which affects a patients vision. Cataracteous lenses are sometimes removed and replaced in a procedure commonly referred to as phacoemulsification. Phaco procedures are typically performed with an ultrasonically driven handpiece which is used to break the lens. The broken lens is removed through an aspiration line that is coupled to the handpiece.

The handpiece has a tip which is inserted through an incision in the cornea. The handpiece typically contains a number of ultrasonic transducers that convert electrical power into a mechanical oscillating movement of the tip. The distal end of the tip has an opening which is in fluid communication with the aspiration line. The oscillating movement of the tip will break the lens into small pieces that are then drawn into the aspiration line through the tip opening.

The handpiece is typically connected to a console that contains a power supply. The power supply provides a driving signal that drives the ultrasonic transducers. To obtain a maximum response from the ultrasonic transducers, the frequency of the driving signal is typically at, or close to, the natural frequency of the transducers. A driving signal at the natural frequency will cause the transducers to operate in a resonant mode.

It has been found that an ultrasonically driven tip will generate heat which may burn or otherwise denature the corneal tissue. The denatured tissue may affect the patients vision. Additionally, the oscillating tip creates turbulence in the surrounding fluid. The turbulent fluid can make it difficult to view the end of the tip and increase the difficulty of performing the procedure. It would be desirable to provide an ultrasonically driven handpiece that can cut tissue but does not generate a significant amount of heat. It would also be desirable to provide a phaco handpiece that does not create a relatively large amount of turbulence during operation.

BRIEF SUMMARY OF THE INVENTION

One embodiment of the present invention is a control circuit that provides a driving signal to a transducer coupled to a mechanical cutting element. The transducer is capable of operating in a resonant mode. The driving signal contains a plurality of pulses provided in a time interval that does not cause the transducer to operate in the resonant mode.

BRIEF DESCRIPTION OF THE DRAWINGS

FIG. 1 is an illustration of an embodiment of a tissue cutting system of the present invention;

FIG. 2 is a schematic of a control circuit of the system;

DETAILED DESCRIPTION OF THE PREFERRED EMBODIMENT

Figure 3:
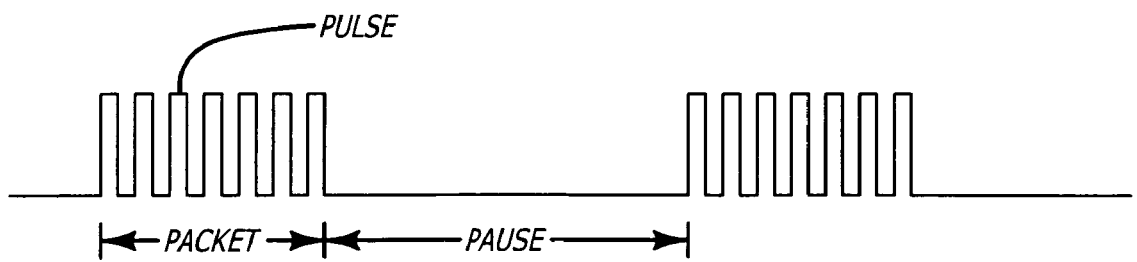
FIG. 3 is a graph showing a driving signal provided by the control circuit; and, FIG. 4 is schematic of an alternate embodiment of a tissue cutting system.

In general the present invention provides a control circuit that provides a driving signal to a transducer that is coupled to a mechanical cutting element. The driving signal has a waveform such that the mechanical cutting element can cut tissue without generating heat. The driving signal contains packets of pulses separated by pauses. Each packet will have a time duration that does not induce a resonant mode of operation for the transducer. The packets do have enough energy to move the cutting element and cut tissue. It has been found that the short duration of pulses will cut tissue without generating any significant amount of heat at the cutting site. Additionally, when used in a fluid environment such as a phaco procedure it was found that the cutting element did not create as much fluid turbulence than devices of the prior art. The reduction in turbulence improves visibility for the surgeon performing the procedure.

Referring to the drawings more particularly by reference numbers, FIG. 1 shows an embodiment of an ultrasonic tissue cutting system 10 of the present invention. The system 10 may include an ultrasonically driven handpiece which has a tip 14 that can be inserted into a cornea 16. The tip 14 may also be referred to as a cutting element. The handpiece 12 may include one or more ultrasonic transducers 18 that convert electrical power into mechanical movement of the tip 14. The handpiece 12 is typically held by a surgeon who performs a surgical procedure with the system 10. By way of example, the system 10 can be used to perform a phacoemulsification procedure to break and aspirate a lens of the cornea 16.

The handpiece 12 is coupled to a pump 20 by an aspiration line 22. The pump 20 creates a vacuum pressure within the aspiration line 22. The aspiration line 22 is in fluid communication with an inner channel 24 and opening 26 in the tip 14. The vacuum pressure within the line 22 can aspirate matter from the cornea 16.

The system 10 may include a control circuit 28 that provides a driving signal to the transducers 18. The control circuit 28 may be located within a console 30 that is connected the handpiece 12. The console 30 may have input knobs or buttons 32 that allow the surgeon to vary different parameters of the system 10. The console 30 may also have a readout display 34 that provides an indication of the power level, etc. of the system 10.

FIG. 2 shows an embodiment of a control circuit 28. The control circuit 28 may include a microprocessor 36 that defines the driving signal provided to the transducers 18. The driving signal may be defined in accordance with a software and/or firmware of the system. The processor 36 may be connected to, or contain, memory 38 which contains instructions and data used to perform software to define the driving signal and operate the system 10. Although a microprocessor 36 is shown and described, it is to be understood that other elements, circuits or devices may be used to generate the driving signal.

The processor 36 may be connected to, or contain, a digital to analog (D/A) converter 40. The D/A converter 40 converts digital bits strings provided by the processor 36 to an analog signal. The D/A converter 40 may be connected to a voltage controlled oscillator (VCO) 42 that converts the analog signal to a driving signal. The frequency of the driving signal is dependent upon the amplitude of the analog signal provided from the D/A converter 40. The driving signal may be amplified by an amplifier 44 before being provided to the transducers 18.

The transducers 18 have a natural frequency. Additionally, the transducers 18 are capable of operating in a resonant mode to provide a maximum output. The handpiece 12 may also include a horn (not shown) that mechanically amplifies the output of the transducers 18.

FIG. 3 shows an example of a driving signal provided to the transducers. The driving signal may include packets of pulses separated by pauses. Each packet may have a duration short enough so that the transducers 18 do not enter a resonant mode of operation. The pulses still have enough energy to induce functional movement of the tip 14. The pauses should be of a duration to avoid resonant operation and the generation of a significant amount of heat.

For phaco handpieces with ultrasonically driven piezoelectric transducers it was found that a packet duration between 0.5–5.0 milliseconds allows the tip to effectively cut tissue without generating a significant amount of heat at the cutting site. Additionally, it was found that a pause duration between 3.5–50 milliseconds provided satisfactory results.

When a phaco handpiece was tested using the above ranges, it was found that the temperature at the cutting site did not rise above 45° C. The best results occurred with a packet duration of 0.5 milliseconds and a pause duration of 3.5 milliseconds for a repetition frequency of 250 hertz (Hz). Because the transducers 18 do not resonate, the effective oscillation frequency of the transducers 18 and accompanying tip 14 is equal to the repetition frequency.

It is desirable to provide a pulse frequency that is the same or close to the natural frequency of the transducers. For example, for transducers with a natural frequency of 20 KHz, it was found that a pulse frequency of 22 KHz provided satisfactory results. In general it has been found that providing short packets of pulses that do not induce resonance in the transducers provides a cutting tool that can cut tissue without generating a significant amount of heat.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

Figure 4:
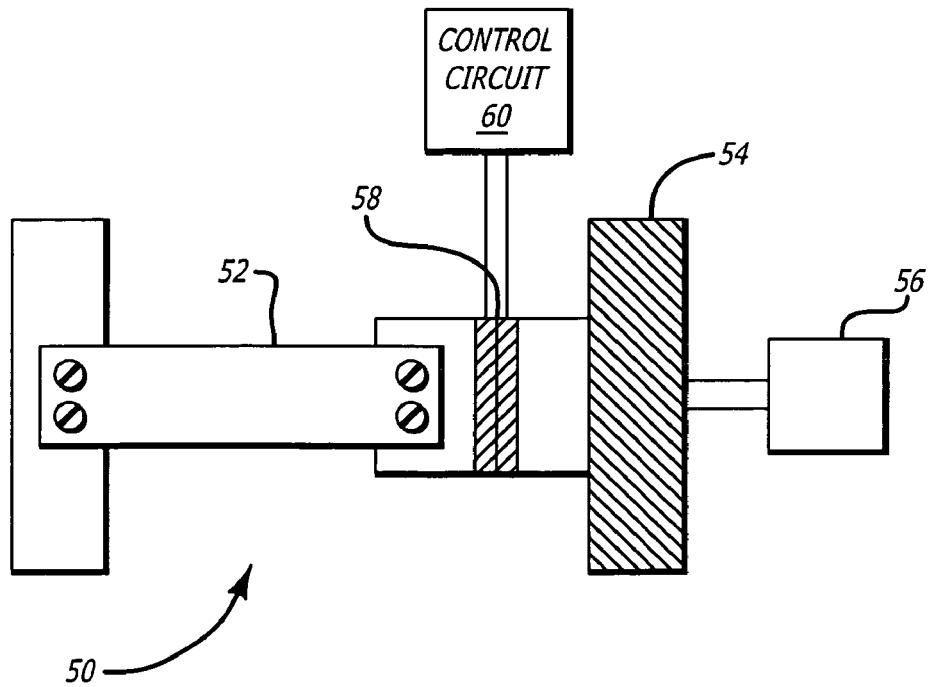

For example, FIG. 4 shows the present invention implemented into a microkeratome 50. The microkeratome 50 is typically used to cut a flap in the cornea to perform a LASIK procedure. LASIK procedures can correct vision by ablating corneal tissue with a laser.

The microkeratome 50 includes a blade 52 that is mounted to a blade holder 54. The blade holder 54 is coupled to a motor 56 that can move the blade 52 across a cornea. The blade 52 may also be connected to transducers 58 that are connected to a control circuit 60. The control circuit 60 may provide a driving signal that causes the blade 52 to move in an oscillating manner. The oscillating motion of the blade 52 will cut tissue while the motor 56 moves the blade across a cornea. The driving signal may be the same or similar to the signal described above and shown in FIG. 3. Such a driving signal will allow the blade 52 to cut without generating heat within the tissue. The generation of heat may denature the cornea and affect the patients vision.

Additionally, the control circuit and resultant driving signal can be used to drive other tissue cutting devices.

What is claimed is:

1. A console that can be coupled to a handpiece that has at least one transducer and a reciprocating tip that can be inserted through a tissue of a patient, comprising:

a control circuit that can be coupled to the tip and generates packets of pulses at approximately a resonant frequency of the transducer to reciprocate the tip, each packet being separated by a pause period of no pulses so that the tip operates in a non-resonant mode and does not generate heat that denatures the tissue.

2. The console of claim 1, wherein each packet has a time duration between 0.5–5.0 milliseconds.

3. The console of claim 2, wherein each pause period has a time duration between 3.5–50 milliseconds.

4. A medical system, comprising:

a handpiece that has at least one transducer and a tip that can be inserted through a tissue of a patient; and, a control circuit that is coupled to said handpiece and generates packets of pulses at approximately a resonant frequency of said transducer to reciprocate said tip, each packet being separated by a pause period of no pulses so that said tip operates in a non-resonant mode and does not generate heat that denatures the tissue.

5. The system of claim 4, wherein each packet has a time duration between 0.5–5.0 milliseconds.

6. The system of claim 5, wherein each pause period has a time duration between 3.5–50 milliseconds.

7. A console that can be coupled to a handpiece that has at least one transducer and a reciprocating tip that can be inserted through a cornea of a patient, comprising:

a control circuit that be coupled to the tip and generates packets of pulses at approximately a resonant frequency of the transducer to reciprocate the tip, each packet being separated by a pause period of no pulses so that the tip operates in a non-resonant mode and does not generate heat that denatures the cornea.

8. The console of claim 7, wherein each packet has a time duration between 0.5–5.0 milliseconds.

9. The console of claim 8, wherein each pause period has a time duration between 3.5–50 milliseconds.

10. The console of claim 7, wherein the temperature does not exceed 45 degrees centigrade.

11. A medical system, comprising:

a handpiece that has at least one transducer and a tip that can be inserted through a cornea of a patient; and, a control circuit that is coupled to said handpiece and generates packets of pulses at approximately a resonant frequency of said transducer to reciprocate said tip, each packet being separated by a pause period of no pulses so that said tip operates in a non-resonant mode and does not generate heat that denatures the cornea.

12. The system of claim 11, wherein each packet has a time duration between 0.5–5.0 milliseconds.

13. The system of claim 12, wherein each pause period has a time duration between 3.5–50 milliseconds.

14. The system of claim 11, wherein the temperature does not exceed 45 degrees centigrade.

15. A medical system, comprising:

a cutting element that can be placed in contact with a tissue of a patient;

a transducer coupled to said cutting element; and, a control circuit that is coupled to said transducer and generates packets of pulses at approximately a resonant frequency of said transducer to reciprocate said cutting element, each packet being separated by a pause period of no pulses so that said tip operates in a non-resonant mode and does not generate heat that denatures the tissue.

16. The system of claim 15, wherein each packet has a time duration between 0.5–5.0 milliseconds.

17. The system of claim 16, wherein each pause period has a time duration between 3.5–50 milliseconds.

18. A medical system, comprising:
- a cutting element that can be placed in contact with a cornea of a patient;
- a transducer coupled to said cutting element; and,
- a control circuit that is coupled to said transducer and generates packets of pulses at approximately a resonant frequency of said transducer to reciprocate said cutting element, each packet being separated by a pause period of no pulses so that said tip operates in a non-resonant mode and does not generate heat that denatures the cornea.

19. The system of claim 18, wherein each packet has a time duration between 0.5–5.0 milliseconds.

20. The system of claim 19, wherein each pause period has a time duration between 3.5–50 milliseconds.

21. The system of claim 18, wherein the temperature does not exceed 45 degrees centigrade.

* * * * *